United States Patent [19]
Strauss et al.

[11] Patent Number: 5,387,397
[45] Date of Patent: Feb. 7, 1995

[54] METHOD AND APPARATUS FOR CONTINUOUS CHEMICAL REACTIONS

[75] Inventors: Christopher R. Strauss, North Balwyn; Alan F. Faux, Footscray, both of Australia

[73] Assignee: Commonwealth Scientific and Industrial Research Organisation, Campbell, Australia

[21] Appl. No.: 892,996

[22] Filed: Jun. 3, 1992

Related U.S. Application Data

[62] Division of Ser. No. 477,963, May 31, 1990, abandoned.

[51] Int. Cl.⁶ .............................................. B01J 8/00
[52] U.S. Cl. ................................. 422/129; 422/186; 422/187; 422/198; 546/296; 546/319
[58] Field of Search ................. 546/296, 319; 422/129, 422/186, 187, 198; 219/10.55 R, 10.55 A

[56] References Cited

FOREIGN PATENT DOCUMENTS 2098040 11/1982 United Kingdom .

*Primary Examiner*—Timothy M. McMahon
*Attorney, Agent, or Firm*—Sughrue, Mion, Zinn, Macpeak & Seas

[57] ABSTRACT

A method and apparatus of conducting chemical reactions on a continuous basis involving feeding a mixture of reactants through a microwave heating zone and controlling the feed rate, feed pressure or microwave power input such that a desired chemical reaction occurs at a predetermined temperature within the feed. Apparatus for performing the method comprises a pump (105) to feed the reactants through a conduit (102, 103, 104) a section of which (103) passes through a microwave heating apparatus (106, 107). The effluent section (104) of the conduit includes a heat exchanger (109) and pressure control means (110). The apparatus is operated under the control of a microprocessor (112) which allows predetermined operating parameters to be set by an operator.

7 Claims, 2 Drawing Sheets

METHOD AND APPARATUS FOR CONTINUOUS CHEMICAL REACTIONS

This is a divisional of application Ser. No. 07/477,963 filed May 31, 1990 now abandoned.

TECHNICAL FIELD

This invention relates to a method and apparatus for carrying out continuous chemical reactions using microwave energy. The invention is particularly applicable for carrying out chemical synthesis reactions.

BACKGROUND ART

Although microwave ovens have been utilised for rapid heating domestically for several years, it is only recently that their use for batchwise organic synthesis has been reported[21-24]. It has been demonstrated that microwave heating can provide a means for dramatically increasing the rate of reactions. In the above synthetic organic chemical publications[21-24] the microwave reactions were carried out in sealed containers usually made of polytetrafluoroethylene (PTFE). Under those conditions, the solvent was rapidly superheated and high pressures developed in the containers, thus enabling the reaction mixtures to reach temperatures greater than those attained at reflux. The rate enhancements observed were attributed[23,24] to these effects of temperature. However severe disadvantages are associated with the published technique.

The reactions have been carried out in sealed vessels often surrounded by vermiculite and housed in an outer container. Such a system prevents observation of the mixture during the reaction and precludes adequate mixing for reactions involving more than one phase. Conventional temperature sensors being metallic can cause arcing and so cannot be used in a microwave oven. There is also no way of measuring the pressures generated in the sealed systems. Reactions thus cannot be carefully monitored and can easily be overheated, creating the potential for overreaction, decomposition and even explosions.

Hot reaction mixtures have also been found to transfer heat to the PTFE containers, softening them. The pressure in the reaction vessel has then caused the walls of the container to deform and rupture explosively on occasions. According to the Canadian group[23] this tended to occur when reaction times were increased in an attempt to reach completion. To try to overcome this problem, Gedye et al.[23] employed PTFE containers with pressure-release caps and recommended that these be filled to only 10–15% capacity and operated at reduced power settings and for limited times (up to 5 minutes). These modifications appear to present fresh difficulties. A potential safety hazard would be created by venting flammable solvents (and reactants) directly into the oven and only low volumes of materials could be reacted at any one time under limited conditions.

Another recognised disadvantage is that the rate of reaction also decreases as the volumes of reagents and solvent increase[1], thus substantially militating against scale-up and restricting the method to small batches.

A flow through microwave catalysis system has been disclosed by Wolf et al.[25]. This known system uses an industrial 2.5 GHz Micro-Aire Oven with a variable power level of 80–1000 watts and a glass reaction cell. In this known system a metal catalyst within the reaction cell is heated by microwaves applied in pulses with appropriate off-time periods to keep the overall temperature of the reaction cell at a desirable range.

U.S. Pat. No. 3,535,482 to JH Kluck discloses microwave apparatus for rapidly heating fluids, namely foods such as fruit juice, soup, puree, etc. for blanching, concentrating, pasteurisation and sterilization. This known apparatus provides a flow through system for continuous processing in which heat is generated directly within the fluid and in which the flow conditions and pressure of the fluid are controllable. The apparatus includes a length of microwave transparent tubing, through which the fluid passes, mounted transversley through a waveguide. As described, the length of the tubing exposed to the microwave energy is made as short as possible such that the amount of fluid being heated at any instant is at a minimum. This requirement imposes restrictions on the diameter of the tube and its location within the waveguide, depending on the nature of the fluid, desired outlet temperature and the frequency of the microwave energy used for the heating. Thus, unlike the apparatus of the present invention, the apparatus described in U.S. Pat. No. 4,535,482 does not permit of precise control, in any one application, of a range of parameters suitable for carrying out chemical reactions on a continuous basis. Furthermore, the requirement that the tube passing through the waveguide be of minimum length and the concommittent short residence time (described as being in the order of 0.1 to 0.01 seconds) of the fluid within the heating zone, would cause the apparatus to be unsuitable for conducting chemical reactions. Also, in this known apparatus the heated fluid is depressurised and vented to atmosphere prior to being cooled, which is an arrangement in which volatile products would be lost were the apparatus to be used for carrying out a chemical reaction.

DISCLOSURE OF THE INVENTION

An object of the present invention is to provide a method and apparatus for conducting continuous chemical reactions in which the above described problems may be avoided and which allows a high degree of control over the reactions.

According to a first aspect of the invention, there is provided a method of performing chemical reactions on a continuous basis comprising:
 i) providing a continuous and pressurized feed of liquid or slurry to and through a microwave heating zone, the feed liquid or slurry including at least one reactant, and a component of the liquid or slurry being capable of absorbing microwave radiation,
 ii) subjecting the feed to microwave energy as it passes through the microwave zone, so as to cause a chemical reaction to occur.

Preferably the chemical reaction is controlled by controlling the temperature of the feed within the heating zone.

Preferably one or more of the pressure or flow rate of the feed, or the microwave power or frequency is controlled such that a desired chemical reaction occurs at a predetermined temperature, the reaction products being entrained in the feed and removed from the microwave zone therewith.

Preferably the reaction product(s) are cooled substantially immediately on passage from the microwave zone.

According to a second aspect of the invention there is provided an apparatus for performing chemical reactions on a continuous basis comprising:

i) liquid transport and containment means having an inlet section, intermediate section and outlet effluent section, ii) supply means to feed a liquid or slurry at a controllably variable rate through the liquid transport and containment means, iii) a microwave generator to supply microwave energy to the intermediate section, iv) temperature measurement means associated with the intermediate or effluent sections to measure the temperature of the product(s) of a chemical reaction, and v) pressure control means, vi) the supply means, temperature measurement means, pressure control means and microwave generator being operably interconnected such that at least one of the variables of flow rate or pressure of a feed liquid or slurry, the microwave energy, or the temperature of a chemical reaction within the feed, is controllably varied in response to variations in another of the variables from a predetermined set value, to thereby maintain said another variable substantially at the predetermined set value.

The apparatus may additionally comprise means for cooling the mixture substantially immediately upon leaving the intermediate section.

Preferably the microwave generator can supply energy of variable power level or frequency. Alternatively, the microwave generator may be switched on and off to provide the controlled energy input.

In another aspect the invention provides apparatus for performing chemical reactions on a continuous basis comprising:

i) liquid transport and containment means having an inlet section, intermediate section and outlet effluent section, ii) supply means to feed a liquid or slurry at a controllably variable rate through the liquid transport and containment means, iii) a microwave generator to supply microwave energy to the intermediate section, iv) temperature measurement means associated with the intermediate or effluent sections to measure the temperature of the product(s) of a chemical reaction, v) pressure control means, and vi) heat exchange means in the effluent section to cool the effluent feed and entrained reaction product(s) substantially immediately on exit from the intermediate section.

Preferably the apparatus includes a device in the effluent section to measure the temperature of the effluent products. This device, which may be a K-type thermocouple, is ideally placed to measure the temperature of the effluent immediately upon exit from the intermediate section of the liquid transport means.

Alternatively the temperature measurement device may be placed within the microwave zone of the apparatus and comprise for example an infrared or fibre optic sensor. This type of device offers the advantage over a thermo-couple, of more accurate measurement because the measurement is actually taken at the reaction zone and not removed therefrom as occurs with a thermo-couple.

The method and apparatus of the invention is particularly suitable for organic synthesis reactions and is especially suitable for the production of labile molecules.

The need to prepare labile molecules under unfavourable conditions of heat has been a severe problem in synthetic chemistry for decades. In many cases the products decompose or polymerize during the synthetic or isolation steps, resulting in greatly diminished yields and, in the worst cases, total loss of product. Alternatively, by-product formation often is a competing process, resulting in undesired compounds which then have to be separated from the products. The method and apparatus of the present invention allows reactants to be rapidly heated and cooled. The continuous flow aspect of the invention also allows for unstable products to be quickly removed from the heat source and rapidly diluted if necessary.

To ensure the rapid cooling of reaction products, the heat exchanger is situated relatively adjacent to the intermediate section; that is, in a position to cool the reaction products as soon as possible after their exit from the microwave zone.

The microwave generator and microwave zone may be a conventional microwave oven or other suitable system, for example, an antenna or waveguide configuration. Such equipment for generating microwaves is well known to those skilled in the art and is not, therefore, described in detail herein.

A variable frequency microwave source allows the frequency of the input radiation to be selected to activate particular molecules and thereby "localize" the heating to specific sites within a feed liquid or slurry, which allows a greater degree of control to be exercised over a synthesis reaction. The invention also allows other parameters such as rate of feed, heat input and pressure to be easily controlled.

The apparatus may include electrical control circuitry wherein the temperature of the treatment, the cooling temperature, the flow rate or the pressure of a feed liquid or slurry within the liquid transport means may be selectively predetermined. Preferably, during operation of the apparatus one or more of such predetermined inputs is maintained at its/their selected values by suitable feedback circuitry to control on or more the liquid transport means may be selectively predetermined. Preferably, during operation of the apparatus one or more of such predetermined inputs is maintained at its/their selected values by suitable feedback circuitry to control one or more of the other variables. For example, the temperature of the treatment can be maintained at a preselected value by altering the microwave power input, or by adjustments to flow rate or pressure, or all three, during the treatment by appropriate feedback control. Such monitoring and feedback control may be carried out by a microprocessor. Furthermore the control circuitry may include a facility to selectively predetermine the time for operation of the apparatus.

Also, according to the present disclosure, the heat exchange means of the apparatus preferably comprises electronic means which avoids the need for liquid or gaseous refrigerants. This electronic means may comprise a Peltier cooling device.

The apparatus of the invention is also suitable for scaling up so as to conduct large industrial scale (compared with laboratory scale) processes.

In apparatus according to the invention there is a negligible radial temperature gradient within the feed liquid or slurry so the material on the walls of a reaction coil (i.e. the intermediate section of the liquid transport means) is not significantly hotter than the body of the feed. The rate of temperature rise can be varied easily by adjusting the microwave power and the response time is very short in comparison with conventional heating. When the power is turned off heat input ceases immediately as there is no thermal inertia in the microwave irradiation zone. At any one time there is a low volume of feed liquid or slurry passing through the irradiation zone so the energy is rapidly absorbed by the feed liquid or slurry. Since there is such a low volume of feed being heated at any one time the apparatus is safe to use when compared with batch reactors. The apparatus also permits observation of the feed as it passes through the irradiation zone.

BRIEF DESCRIPTION OF THE DRAWINGS

The invention will now be described, by way of example only, with reference to the accompanying drawings, in which.

BEST MODES FOR CARRYING OUT THE INVENTION

Figure 1:
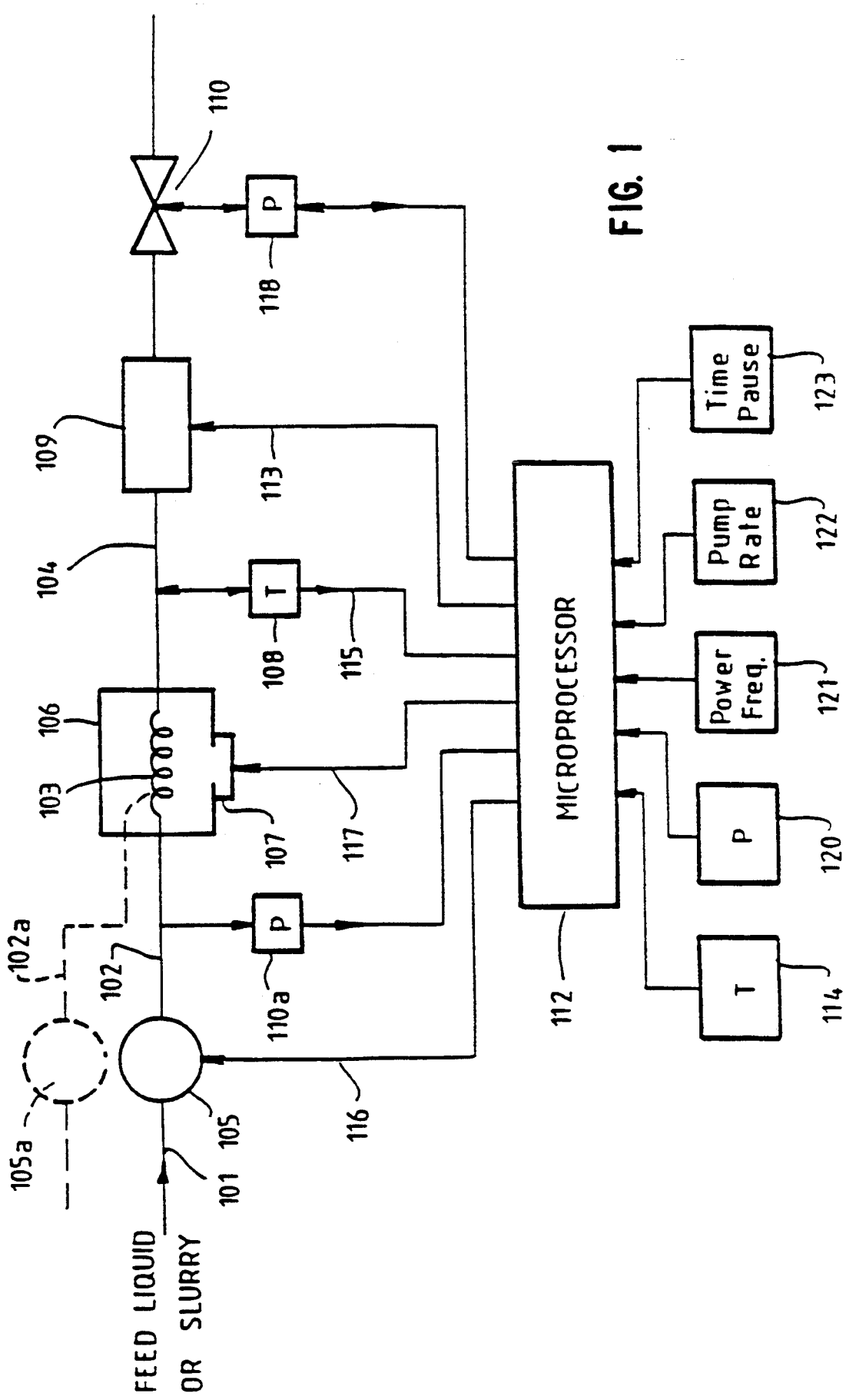
FIG. 1 is a block diagram illustrating the components of apparatus according to the invention.

FIG. 1 is a schematic block diagram illustrating the components of apparatus according to the invention and a control arrangement therefor. The apparatus comprises a flow-through liquid transport and containment means such as conduit 101 having an inlet section 102, intermediate section 103 and outlet or effluent section 104. The inlet section 102 includes a pump 105 that is controllably variable to deliver a feed liquid or slurry through conduit 101 at desired flow rates and pressures, and a pressure sensor 110a. Additional inlet conduits (e.g. 102a) and pumps (e.g. 105a) may be provided to allow different reactants to be separately supplied for mixing within the intermediate section 103. The intermediate section 103 of conduit 101 is contained within a microwave heating zone 106 to which microwave energy of variable power or frequency is supplied by microwave generator 107. The microwave heating zone may consist of a suitable cavity adapted to permit observation of a reaction mixture as it passes through the intermediate section 103 of conduit 101. The intermediate section 103 of conduit 101 must be made of a material that is substantially transparent to microwaves.

The outlet or effluent section 104 of conduit 101 includes a temperature sensing means 108 positioned such that the temperature of the feed liquid or slurry and entrained reaction product(s) is measured virtually immediately upon exit of such feed and products from the intermediate section 103. The temperature sensing means is so positioned because it is highly desirable that the temperature at which the chemical reaction within the feed occurs be determined to allow as high a degree of control as possible over a reaction. Another possibility to ensure an accurate measurement of the temperature of a reaction is to use a fibre optic or infra-red temperature sensing device positioned to measure the temperature of the products within the intermediate section 103.

After the temperature sensing means 108, the outlet or effluent section includes a heat exchange means 109. Preferably the cooling temperature of this means is electronically controlled, for example, by use of a Peltier cooling device, to avoid the use of liquid or gaseous cooling fluids or refrigerants. Following the heat exchanger, the outlet effluent section 104 includes a pressure control means 110 to allow a feed liquid or slurry to be conveyed through the apparatus under adjustable pressures.

The apparatus includes a control means, such as microprocessor 112, operably interconnecting the pump 105, microwave generator 107, temperature sensing means 108 and pressure sensing means 110a and pressure control means 110. The control means 112 may also supply power as shown at 113 to a Peltier cooling device of heat exchanger 109. Microprocessor 112 includes the facility to selectively input predetermined operating parameters for the apparatus. Thus, an operator may preset the temperature for a reaction by the temperature setting means 114, and the microprocessor compares this set signal with a signal 115 from temperature sensor 108 to determine a difference signal which in turn is used to control any one or more of the inputs 116 (to the pump 105), 117 (to the microwave generator 107), or 118 (to the pressure control means 110) so as to vary the feed rate, microwave power level, microwave frequency or pressure to minimise the temperature difference signal and thereby maintain the temperature at the set value.

Other selectively settable inputs to the microprocessor 112 may be a pressure level 120, microwave power level or frequency 121, and feed rate 122. A feedback arrangement, similar to that described above for temperature control, may also be included to maintain the pressure of a reaction to a predetermined set level. The microprocessor 112 may also include a facility 123 to input to set time for operation of the apparatus.

Figure 2:
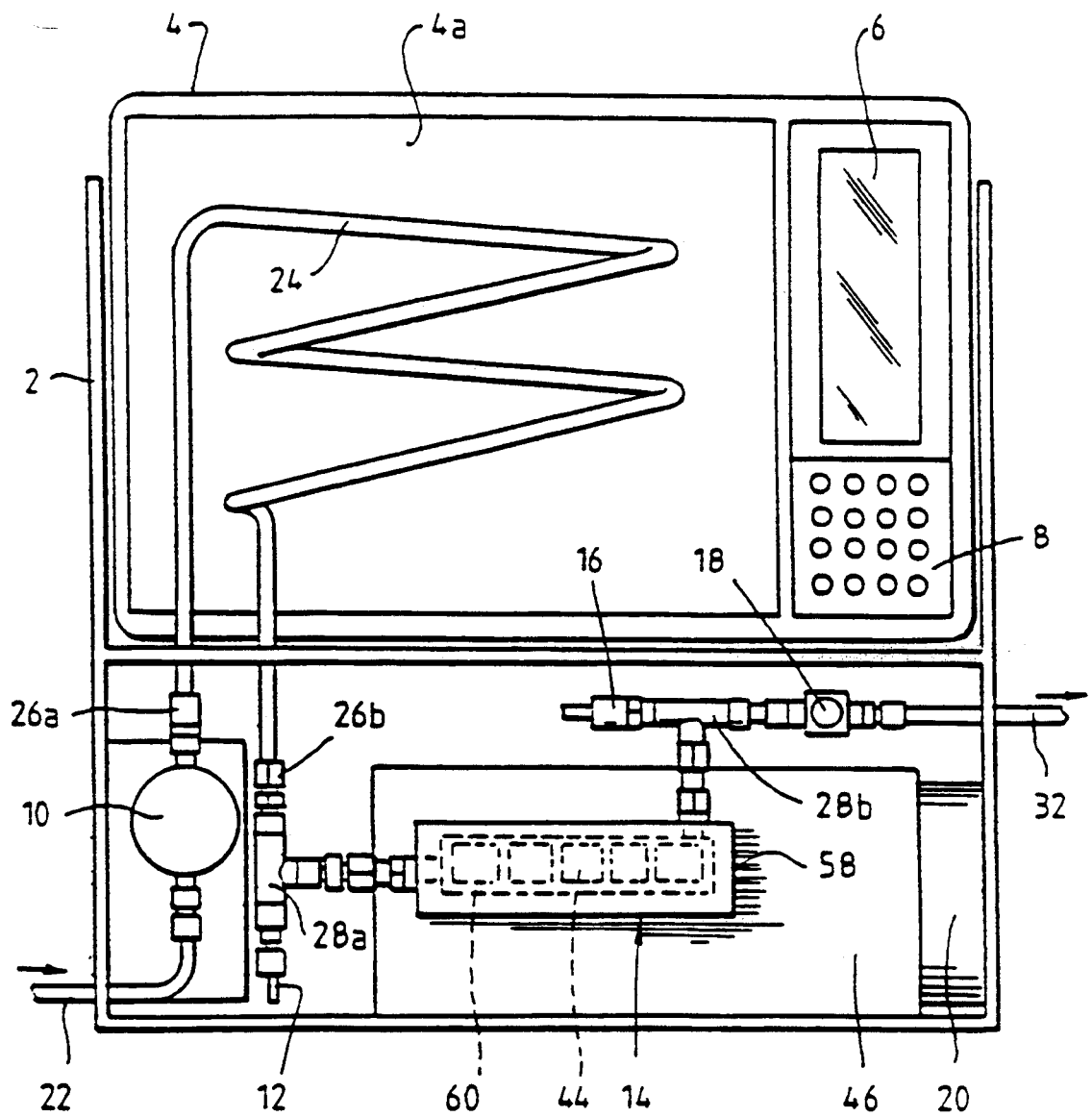
FIG. 2 is a front elevational schematic view of an embodiment of apparatus according to the invention.

FIG. 2 shows the layout of a microwave heating apparatus of the invention suitable for bench top laboratory use. The apparatus comprises a frame 2 (for mounting the various components of the apparatus) the upper section of which carries a microwave enclosure 4, associated magnetron (not shown) and control circuitry. The right hand margin of the microwave enclosure 4 includes a display 6, for example a liquid crystal display, which depicts operating parameters in real time as well as preset operating conditions. A touch pad 8 located below the display allows a set of operating parameters to be entered into a memory of the apparatus. The magnetron and suitable electronic control circuitry may be mounted to the right hand side of the enclosure 4 behind the display 6 and touch pad 8. The electronic control may include an appropriately programmed microprocessor or dedicated circuitry.

The bottom section of frame 2 mounts the control devices of the flow through system. These control devices comprise feed pump 10 (for example a diaphragm metering pump capable of delivering 25 ml/min at 1200 KPa), thermocouple 12, cooling (heat exchange) means 14, pressure sensor-transducer 16 and pressure control valve 18 (for example a solenoid operated valve). The pressure control valve may be manually adjustable. A fan 20 is associated with the cooling means 14. The flow through system thus comprises an inlet end 22 connected to feed pump 10, the output of the pump being connected to an intermediate feed tube section 24 by a suitable connector 26a. The intermediate section 24 of the tube passes through the bottom wall of enclosure 4, into the cavity 4a of the microwave enclosure 4 and then passes out of the cavity through the bottom wall to another connector 26b.

The intermediate section 24 may be easily removed and replaced by alternative sections of different material or configuration by disconnection and reconnection at connectors 26a and 26b. The material of intermediate section 24 may be any microwave transparent material suitable for the particular reaction or other task being undertaken within the apparatus. PTFE or borosilicate glass are particularly suitable. The intermediate section 24 may also be of any configuration and dimensions suitable for the task at hand. A preferred configuration is a coil and chemical reactions using coils made of PTFE tubing of various lengths, with an outside diameter of 6 mm and inside diameter of 3 mm have been used to carry out various chemical reactions at temperatures as high as 200° C. Such a material and configuration has been found to be particularly suitable in achieving the result that the microwave energy heats substantially only the feed liquid or slurry within the intermediate section.

A T-junction 28a is fitted to connector 26b, the thermocouple 12 being mounted in one arm of the T-junction. The other arm of the T-junction 28a is connected to the inlet of the cooling means 14. The outlet of the cooling means is connected to another T-junction 28b, in one arm of which is mounted the pressure transducer 16. The other arm of T-junction 28b leads to outlet 32 via the pressure control valve 18.

The layout depicted in FIG. 2, besides providing a compact and easily moveable heating apparatus, also allows the total volume of the tubing to be kept to a minimum such that only a small quantity of sample is being processed at any instant. This avoids waste and provides added safety. It should be noted, however, that other constructions, for example a modular assemblage, are possible.

Connectors 26a and 26b, T-junctions 28a and 28b, the inlet and outlet fittings of feed pump 10, the cooling means 14 and the pressure control valve 18 may be of stainless steel and lined with PTFE.

The electronic heat exchange means 14 may comprise a number of Peltier cooling pads 44 mounted in heat conducting relationship to a side of a heat sink 46. The pads 44 may extend along the length of a cooling chamber 60 formed within block 58. Peltier pads which can provide a temperature gradient of 65° C. across their opposite faces are suitable for the present apparatus. Preferably the surfaces of the cooling chamber 60 which contact the reaction products are coated with PTFE. In operation, heat sink 46 may be maintained at about 60°-75° C. (by intermittent or continuous operation of fan 20 as appropriate) such that a temperature differential of (say) 65° C. between the faces of Peltier pads 44 will produce a cooling temperature of about −5° to 10° C. at block 58 and thus within chamber 60. That is, the reaction products within intermediate section 24, which may be at 200° C., on leaving the microwave cavity enter (via T-junction 28a) the chamber 60 and thus may encounter a cooling temperature of between −5° to 10° C. The actual cooling temperature may, of course, be preset and monitored by appropriate control circuitry.

Examples of reactions that have been carried out using the above described apparatus are: oxidation, nucleophilic substitution, addition, esterification, transesterification, acetalisation, transketalisation, amidation, hydrolyses, isomerisation, condensation, decarboxylation and elimination.

Details of some of these reactions are now described below.

EXPERIMENTAL

General

Unless stated otherwise, the microwave apparatus according to the invention was fitted with a PTFE coil, 3 meters long, 6 mm o.d. and 3 mm i.d., with a volume of 23.8 ml (this coil constituting the intermediate section of the liquid transport means). Reaction conditions are given in parentheses in the order, flow rate in ml/min., temperature in °C., and pressure in kilopascals (kPa).

Spectral data for synthetic products agreed with those in the literature. As all the compounds prepared here are well documented, these data have not been presented.

Solvents were commercially available analytical grade and were not further treated before use.

Table 1 illustrates some of the reactions described below.

SYNTHETIC DETAILS

Preparations of esters.

1. n-Butyl acetate

A solution of n-butanol (74 g; 1.0 mole) and glacial HOAc (120 ml; 2 mole) containing conc. sulphuric acid (2 ml) was passed through the reaction coil (10.5 ml/min., 152°-7° C., 600-630 kPa). The product (89 g; 77% yield), b.p. 123°-4° C. was extracted and distilled according to ref.[1], in which a yield of 69% was reported after 6 hours at reflux.

2. Isopropyl acetate

A solution of isopropanol (40 g; 0.7 mole), glacial HOAc (160 g; 2.5 mole) and conc., sulphuric acid (2 g) was pumped through the apparatus of the invention (which is sometimes referred to below as a Continuous Microwave Reactor (CMR) (10.5 ml/min., 154°-8° C., 970 kPa.). The ester (66 g; 98% yield based on the starting alcohol) was obtained after work-up according ref.[2], in which a yield of 46% was obtained after 24 hours at reflux.

3. Methyl Benzoate

A solution of benzoic acid (30 g; 0.25 mole in MeOH (80 g; 2.5 mole) and conc. sulphuric acid (2.7 ml) was passed through the CMR (10.5 ml/min.; 141°-5° C.; 760 kPa). Excess MeOH was removed by rotary evaporation and the residue poured into water (250 ml) and the product extracted in CCl$_4$. The organic phase was washed with bicarbonate solution, dried over MgSO$_4$, filtered, evaporated, and the product (18.6 g; 56% yield) distilled under reduced pressure; b.p. 109° C./30 mm of Hg. cf ref.[3], where a different method of work-up was used, and a yield of 92% was obtained after 4 hours at reflux.

4. Methyl crotonate

This was prepared in the CMR (10.5 ml/min.; 160°-5°; 760 kPa) from a solution of crotonic acid (43 g; 0.5 mole), MeOH (95 ml; 2.3 mole) and conc. sulphuric acid (3 ml). After work up and distillation the ester (20.2 g), b.p. 118°-20° C. was obtained in 40% yield; cf ref.[4], where a yield of 68% was obtained after 12 hours at reflux.

5. Methyl 2,4,6-trimethylbenzoate

Owing to the steric effects caused by the methyl groups on the 2- and 4-positions of the benzene ring, esterification of 2,4,6-trimethylbenzoic acid is difficult to achieve by conventional means.

2,4,6-Trimethylbenzoic acid (40.4 g.) was mixed with methanol (50 ml) and the solution acidified with sulphuric acid (1.4 ml), and passed through the CMR (15.5 ml/min., 162°–5° C., 1000 kPa). After four successive passes (total residence time 6 min.), the solution was found to contain 11% methyl 2,4,6-trimethylbenzoate by $^1$H NMR.

EXAMPLE OF ESTERIFICATION WITHOUT ADDITION OF CATALYST

Preparation of Ethyl acetate

To achieve esterification by conventional chemical means, a catalytic amount of a strong acid is commonly used and it is difficult to effect esterification between acid and alcohol if a catalyst is not used. A solution containing an 8:1 molar ratio of acetic acid and ethanol was pumped through the CMR (13 ml./min.; 130°–150° C.; 1200 kPa) and the effluent analysed by $^1$H NMR. A 16% conversion of ethanol to ethyl acetate was found. When the molar ratio of acetic to ethanol was altered to 20:1, a 20% conversion was obtained.

HYDROLYSIS OF AN ESTER

Base catalysed hydrolysis of methyl benzoate.

A mixture of methyl benzoate (10.0 g; 74 mmole) and 5% aqueous NaOH solution (100 ml) was passed through the CMR (15 ml/min.; 174°–82° C.; 690–1000 kPa). The resultant solution was acidified with dilute HCl and the benzoic acid extracted into ether. The organic phase was dried with MgSO$_4$, filtered and evaporated to dryness to afford the product (8.5 g) m.p. 122°–3° C. in 95% yield. This reaction has been carried out batchwise by microwave heating, but a higher concentration of sodium hydroxide solution (ie 25%) was used[5].

TRANSESTERIFICATION

Conversion of ethyl benzoate to methyl benzoate under acid catalysis

A solution of ethyl benzoate (23.5 g), MeOH (63.4 ml) and conc. sulphuric acid (2.0 ml) was pumped through the CMR (15 ml/min., 160°–5° C., 900 kPa). The composition of the effluent was determined by GC-MS to be 60% starting material and 40% product. Two further passes of the material through the system resulted in the starting material to product ratio decreasing to 54:46 and then 52:48 respectively.

CONVERSION OF AN ESTER TO AN AMIDE

Preparation of succinamide

A mixture of dimethyl succinate (9.6 g) and 25% aqueous ammonia solution (50 ml) was stirred vigorously and passed through the CMR (23 ml/minute; 133°–5° C.; 800–900 kPa). The product was allowed to crystallise in the cold over 2 hours and was filtered off, washed with a little cold water and dried to afford colourless crystals (4.0 g; 51% yield), m.p. 253°–4° C. with decomposition, cf lit.[6], in which an 88% yield was obtained after 24 hours at ambient temperature.

EXAMPLES OF MANNICH REACTIONS (a) Preparation of Gramine

To dimethylamine (42.5 ml; 0.236 mole), cooled in an ice bath, was added cold glacial HOAc (30 g), followed by 37% formalin (17.2 g; 0.2 mole). This mixture was poured onto indole (23.4 g; 0.2 mole) and water (10 ml) used to rinse out the flask. The mixture was passed through the microwave system (20.5 ml/min.; 160°–70° C.; about 690 kPa). The acetate salt of the product tended to crystallise out rapidly when cooled, so the product was not cooled whilst in the system. The hot effluent from the reaction coil was passed into an Erlenmeyer flask which was placed in an ice bath. The free base was liberated by pouring into a solution of KOH (40 g) in water (300 ml). After 2 hours the crystalline gramine was filtered at the pump and dried to constant weight (34.5 g; 99% yield). According to ref.[7] a comparable yield (97.5%) was obtained by allowing the reaction mixture to stand at 30°–40° C. overnight.

(b) Preparation of dimethylaminopropiophenone hydrochloride

A mixture of acetophenone (100 g), paraformaldehyde (25 g) and dimethylamine hydrochloride (68 g) was vigorously stirred and pumped through the CMR (23 ml/min.; 180°–90° C.; 400 kPa). The product tended to crystallise rapidly when cooled, so was collected by passing the hot effluent into a flask which was cooled in ice-water. Analysis by $^1$H nmr indicated a 44% conversion of acetophenone to product, which was isolated in 29% yield. By conventional methodology[8], a crude yield of 71% can be obtained after 2 hours at reflux followed by overnight refrigeration.

(c) Preparation of 5-Methyfurfuryldimethylamine

Cold glacial HOAc (40 ml) was added slowly to cold 26% aqueous dimethylamine (45 ml) held in an ice bath. Formalin (37%; 18 ml) and 2-methylfuraN (18 ml; 0.2 mole) were added to form two-phase reaction mixture, which was vigorously stirred and pumped through the CMR (20.5 ml/min; 154°–60° C.; 400 kPa;).

The product mixture was poured onto cold aqueous NaOH solution (50 g in 160 ml of water) and the organic phase separated and analysed by GC-MS and $^1$H NMR. A conversion of 66% was obtained. In the conventional preparation, the reaction mixture was heated on a steam bath for four hours and held at room temperature for an additional twenty four hours[9].

(d) Preparation of N,N-dimethyl-2-(2-furoyl)ethylamine hydrochloride

2-Acetylfuran (13.8 g), dimethylamine hydrochloride (13.3 g), paraformaldehyde (5.0 g) and ethanol (80 ml) acidified with concentrated HCl (1.0 ml) were stirred. Part of this mixture (27 ml) was pumped through the CMR (18 ml/min; 160°–70° C.; 500 kPa;) and the hot product collected in an ice-water cooled flask, to afford pale yellow crystals m.p. 172.5°–173° C. (cf lit.[10] m.p. 173°–4° C.) in 13% yield.

EXAMPLE OF ACETAL FORMATION

Preparation of the diethyl acetal of p-chlorobenzaldehyde

A solution of p-chlorobenzaldehyde (14.0 g; 0.1 mole) in absolute EtOH (100 ml), containing p-toluenesulphonic acid (0.5 g) was passed through the CMR (15.5 ml/minute; 114°–6° C.; 700–800 kPa). The reaction mixture was collected in a flask containing NaHCO$_3$ (1 g) and equipped with a magnetic follower. After work up and distillation the acetal (9.3 g) b.p. 144°–6° C./20 mm Hg was recovered in 43% yield of (cf ref.[11]).

EXAMPLES OF NUCLEOPHILIC SUBSTITUTIONS (1) Preparation of benzyl phenyl ether A mixture of sodium phenolate trihydrate (10.2 g; 60 mmole) and benzyl chloride (6.4 ml; 56 mmole) in methanol (150 ml) was pumped through the system (15 ml/minute; 146°–7° C.; 1000–1050 kPa). The MeOH was rotary evaporated off and the residue recrystallised from EtOH to afford colourless needles of phenyl benzyl ether (6.9 g; 67% yield), m.p. 36°–36.3° C.

(2) Preparation of Ortho-formylphenoxyacetic acid

A solution of NaOH (13.3 g; 0.33 mole) in water (34.4 ml) was carefully added, with cooling, to a mixture of chloroacetic acid (15.8 g; 0.17 mole) and salicylaldehyde (20.3 g; 0.17 mole) in water (134 ml). The mixture was heated to 75° C. with magnetic stirring to facilitate dissolution. The warm solution was pumped through the CMR (15 ml/minute; 170°–2° C.; 700 kPa) and carefully acidified with conc. HCl (32 ml). After steam distillation to recover unreacted salicylaldehyde (6.0 g), the residue was cooled and the product, m.p. 130°–1° C., crystallised, filtered off and dried (7.9 g; 37% yield based on consumed salicylaldehyde). For a conventional preparation see ref.[12].

(3) Preparation of 2-Naphthoxyacetic acid from 2-Naphthol.

A mixture of 2-naphthol (6.0 g; 0.04 mole) in 10% NaOH solution (90 ml) and 50% aqueous chloroacetic acid (15 ml) was stirred and heated to 50° C. until dissolution occurred. The warm solution was passed through the CMR (15 ml/min., 155°–6° C., and 300–400 kPa) but not cooled within the system as it tended to precipitate rapidly. Rather, the hot solution after exit was collected in an erlenmeyer flask held in an ice bath. Water (60 ml) was added and the solution acidified with HCl and extracted three times with Et$_2$O. The organic phase was washed with water and the product extract into 5% sodium carbonate solution. The aqueous base was reacidified and the precipitated 2-naphthoxyacetic acid filtered off and recrystallised from water to afford colourless needles (1.4 g; 17% yield), m.p. 153.6°–154° C. For batchwise synthesis by microwave heating, see ref.[5].

Acid catalysed isomerisation of carvone (a) L-Carvone (50 g) and 1M sulphuric acid solution (250 ml) were vigorously stirred to generate an emulsion and this was passed four times through the CMR (15.5 ml/min, 165°–73° C., 690–760 kPa). The reaction mixture was passed through the system four times and analysed by GC after each pass. After successive passes the conversions were 15%, 42%, 56% and 64% respectively, with negligible by-product formation.

(b) Aqueous 0.5M sulphuric acid (25 ml), Teric N100 emulsifying agent (a product of ICI; 2.5 g) and carvone (50 g) were stirred and the emulsion passed through the CMR four times (15.5 ml/min, 165°–75° C., 690–760 kPa). Analysis was again by GC after each pass. After four passes a conversion of 50% was obtained. This experiment was then repeated using 1M sulphuric acid, and was directly comparable with experiment (a) above, the variation being the addition of the emulsifying agent. After four successive passes, the percentage of carvacrol obtained was 32%, 63%, 73% and 83%, with negligible by-product formation.

A conventional method for carrying out this isomerisation [13], gave a 40% conversion after 4 hours heating on a steam bath.

PREPARATION OF AN ENAMINE 4-(1-Cyclohex-1-enyl)morpholine

Morpholine (157 g; 1.8 mol.) and cyclohexanone (147 g; 1.5 mol.) were mixed with toluene (300 ml). Finely ground p-toluenesulphonic acid (1.5 g) was then added and the mixture stirred and pumped through the CMR (15 ml/min.; 103°–4° C.; 1000–1200 kPa). The yield of 4(1-cyclohex-1-enyl) morpholine was estimated by GC-MC as 25%; cf lit.[14].

Depolymerisation of paraformaldehyde

Paraformaldehyde (100 g) was mixed with water (300 ml) and concentrated hydrochloric acid (3 ml). This mixture was stirred vigorously and pumped through the CMR (about 13 ml/min; 150°–170° C.; 1000 kPa), yielding a clear solution (380 ml) containing 25% formaldehyde as determined by wet chemical analysis.

EXAMPLE OF A HOFMANN ELIMINATION

Preparation of Phenyl vinyl ketone

N-(2-benzoylethyl)-N,N,N-trimethylammonium iodide (5.0 g) was suspended in water (400 ml) and the mixture passed through the CMR (15 ml/min; 90°–95° C.; atmospheric pressure) and the hot product collected in a mixture of ice (250 g) and diethyl ether (100 ml), in a flask which was cooled in an ice bath. The ether phase was separated and the aqueous extracted with ether (3×150 ml). The pooled organic phase was dried over anhydrous sodium sulphate and evaporated to dryness, affording phenylvinyl ketone as a colourless oil (1.95 g; 94% yield) in high purity, according to the $^1$H NMR spectrum; cf ref.[15], where a yield of 51% was obtained.

Preparation of 1,2-Dimethyl-3-hydroxypyrid-4-one.

Maltol (i.e. 2-methyl-3-hydroxypyran-4-one) 250 g) was dissolved in 25% aqueous methylamine (750 ml) and water (125 ml). The solution was pumped through the CMR (18 ml/min; 160°–2° C.; 900 kPa) and the hot reaction mixture passed directly into acetone (2.5 liters), cooled in an ice water bath. The crystalline product (146 g; 53% yield) was collected by filtration, and washed with acetone (2×250 ml). The corresponding literature method[17] involved 6.5 hours at reflux, followed by laborious work up.

EXAMPLE OF A KNOEVENAGEL REACTION

Preparation of 3-(2-furanyl)-2-propenoic acid

Malonic acid (104 g; 1 mole) was dissolved in a mixture of furfural (96 g; 1 mole), pyridine (72 ml) and ethanol (10 ml) and pumped through the CMR (15 ml/min; 165° C.; 1200 kPa). The product mixture was diluted with diethyl ether (200 ml) and washed with 5% aqueous sulphuric acid (4×200 ml) to remove most of the pyridine. The remaining solution was evaporated to dryness on a rotary evaporator and the resultant 2-furanacrylic acid (25 g; 18% yield) crystallised from water m. p. 141° C. The MS was in close agreement with spectrum in the MS library. For a convention preparation see ref.[18].

PREPARATION OF OXIMES (a) Citronellal oxime.

Citronellal (5.9 ml) was added to a mixture of hydroxylamine hydrochloride (3.2 g) in water (100 ml) containing sodium hydrogen carbonate (8.4 g) and the material pumped through the CMR (20.5 ml/min; 137°–40° C.; 500–550 kPa). GC-MS showed a 95% conversion to a mixture of the two oximes. For a comparable conventional preparation see[19].

(b) Benzophenone oxime

A solution of benzophenone (10.0 g), hydroxylamine hydrochloride (10.0 g), pyridine (50 ml), and absolute ethanol (50 ml) was pumped through the CMR (15 ml/min; 155°–60° C., 700 kPa). The effluent was cooled and the solvent removed by rotary evaporation, and the residue stirred with cold water (50 ml). The crued oxime was filtered off and recrystallised from ethanol to afford pure product (8.0 g; 73% yield), m.p. 140.5°–141° C., cf lit.[5] for a batchwise preparation by microwave heating.

Reaction of chromotropic acid and formaldehyde

A solution of chromotropic acid (2.8 g) dissolved in water (300 ml) and 2.8 ml of 37% formalin was pumped through the CMR (15 ml/min; 128°–140° C.; 100 kPa–1100 kPa). A dark red solution was produced and this was evaporated to dryness affording a glass with similar physical properties to those in ref.[20], where the corresponding reaction was carried out for one week at room temperature.

Those skilled in the art will appreciate that the invention described herein is susceptible to variations and modifications other than those specifically described. It is therefore to be understood that the invention includes all such variations and modifications which fall within its spirit and scope.

References

1. Vogel's Textbook of Practical Organic Chemistry, Fourth ed; revised by B. S. Furniss, A. J. Hannaford, V. Rogers, P. W. G. Smith and A. R. Tatchell; pub. Longman, New York, (1978), p. 504.
2. ibid., p. 505.
3. ibid., p. 841
4. ibid., p. 506
5. R. N. Gedye, F. E. Smith and K. C. Westaway, Can. J. Chem. 66, 17 (1988).
6. Vogel's Textbook of Practical Organic Chemistry, Fourth ed; revised by B. S. Furniss, A. J. Hannaford, V. Rogers, P. W. G. Smith and A. R. Tatchell; pub. Longman, New York, (1978), p.518.
7. ibid., p.816.
8. ibid., p.815
9. E. L. Eliel and P. E. Peckham, J. Am. Chem. Soc., 72, (1950) 1209.
10. A. Labidi, M-Ch. Salon and A. Gandini, Polymer Bull. 14 (1985) 271.
11. J. M. Sayer and W. P. Jencks, J. Am. Chem. Soc., 99 (1977) 465.
12. A. W. Burgstahler and L. R. Worden, Organic Synthesis Collective Vol. V., H. E. Baumgarten, ed; pub. John Wiley and Sons, New York, 1973. p.251.
13. A Sattar, R. Ahmad, and S. A. Khan, Pakistan J. Sci, Res. , 23 (1980) 177.
14. S. Hunig, E. Lucke and W. Brenninger, Org. Syn., 41, (1961) 65.
15. Vogel's Textbook of Practical Organic Chemistry, Fourth ed.; revised by B. S. Furniss, A. J. Hannaford, V. Rogers, P. W. G. Smith and A. R. Tatchell; pub. Longman, New York, (1978), p. 816.
17. G. J. Kontoghiorges and L. Sheppard, Inorg. Chim. Acta, 136, (1987). L11.
18. S. Rajagopalan and P. V. A. Raman, Organic Synthesis Collective Vol. III, E. C. Horning ed; pub. John Wiley and Sons, New York (1955), p.425.
19. D. Arigoni and O. Jeger, Helv. Chim. Acta, 37, (1954), 881.
20. B. L. Poh, C. S. Lim and K. S. Khoo, Tet, Lett., 30, (1989), 1005.
21. R. Gedye, F. Smith, K. Westaway, H. Ali, L. Baldisera, L. Laberge and J. Rousell Tet. Lett. 27, 279 (1986).
22. R. J. Gigure, T. L. Bray and S. M. Duncan Tet. Lett. 27, 4945 (1986).
23. R. N. Gedye, F. E. Smith and K. C. Westaway, Can J. Chem. 66, 17 (1988).
24. M. S. F. Lie Ken Jie and C. Yan-Kit, Lipids 23, 367 (1988).
25. K. Wolf, H. K. J. Choi and J. K. S. Wan, AOSTRA Journal of Research 3, 53 (1986).

TABLE 1

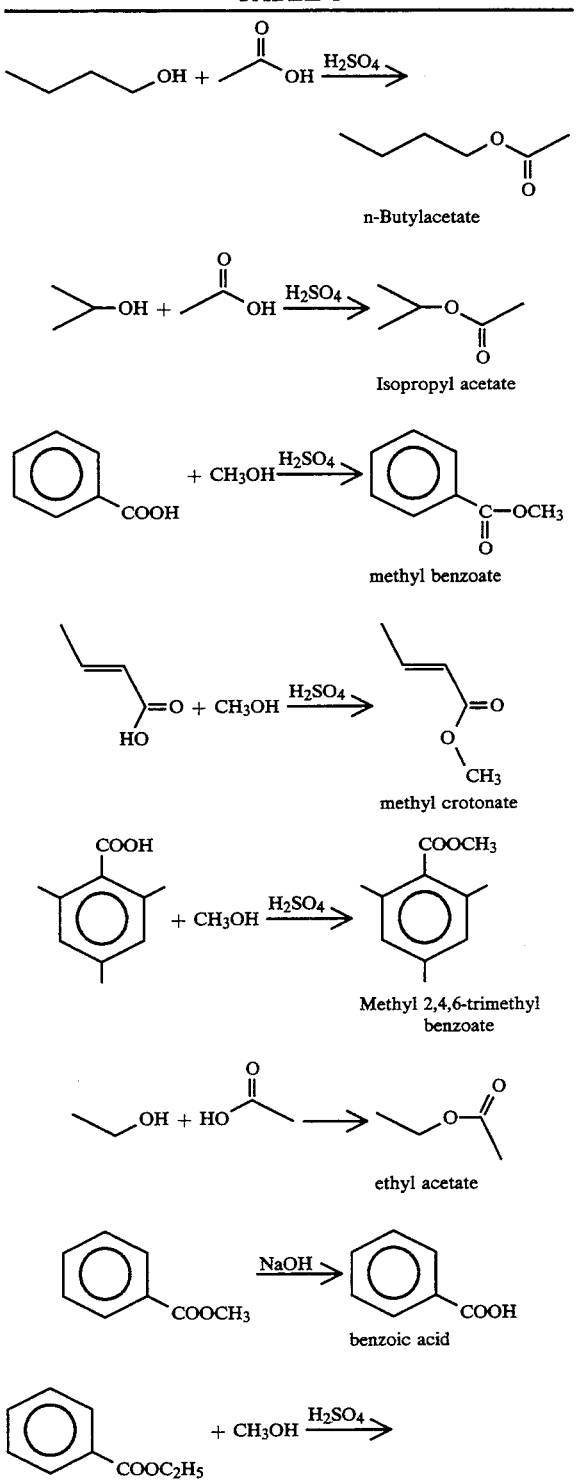

TABLE 1-continued
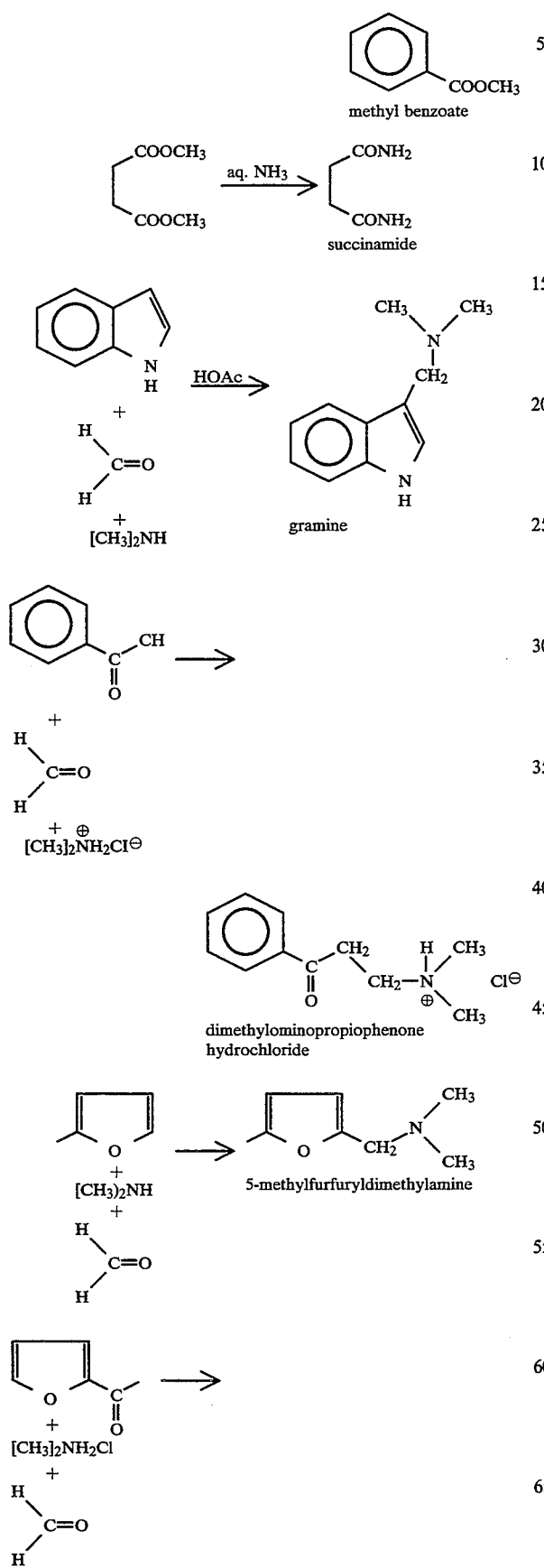
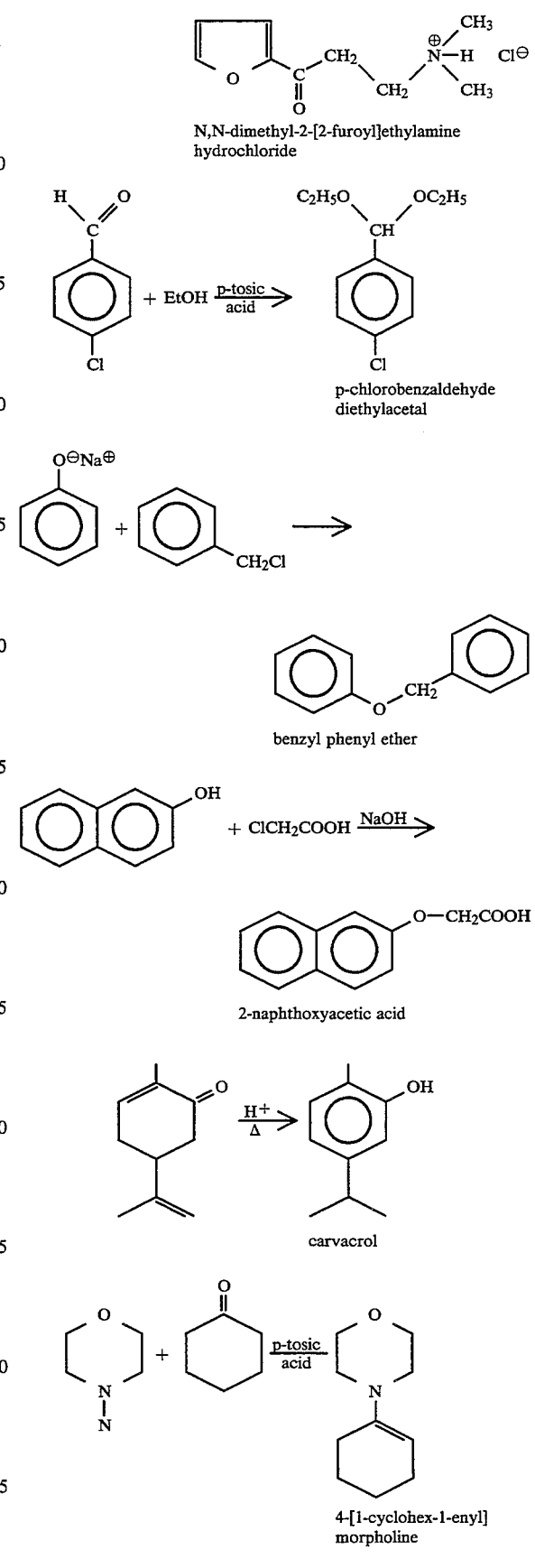

TABLE 1-continued

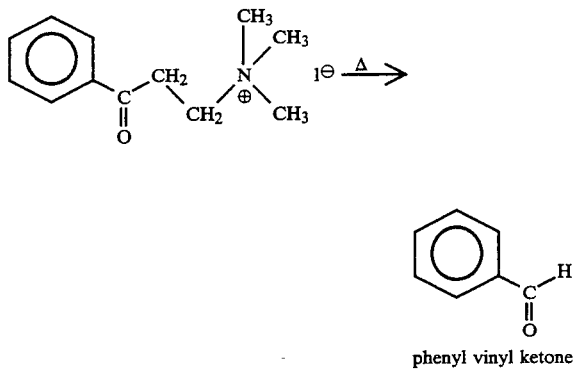

phenyl vinyl ketone

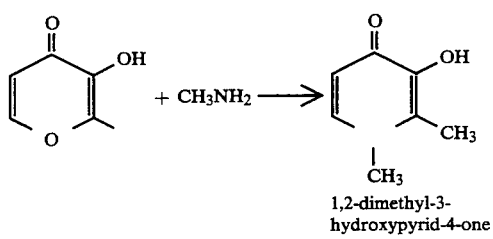

1,2-dimethyl-3-hydroxypyrid-4-one

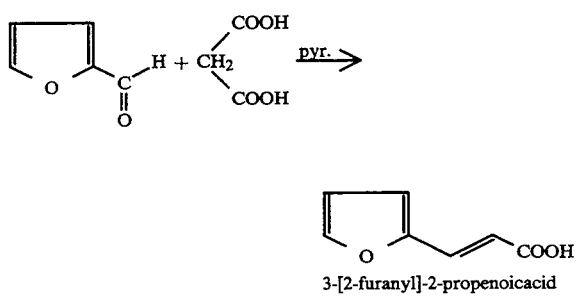

3-[2-furanyl]-2-propenoicacid

PREPARATION OF
ORTHO-FORMYLPHENOXYACETIC ACID

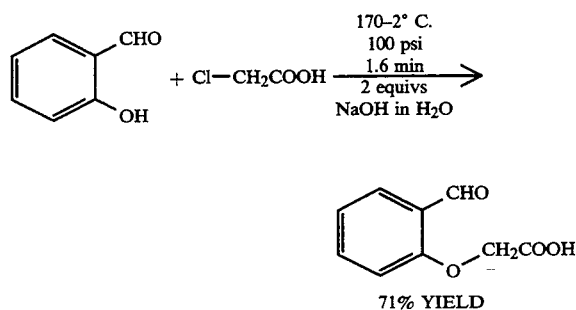

71% YIELD

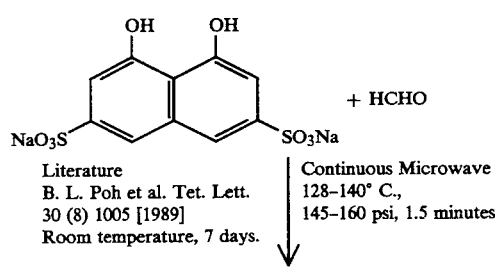

| Literature | Continuous Microwave |
|---|---|
| B. L. Poh et al. Tet. Lett. | 128–140° C., |
| 30 (8) 1005 [1989] | 145–160 psi, 1.5 minutes |
| Room temperature, 7 days. | |

TABLE 1-continued

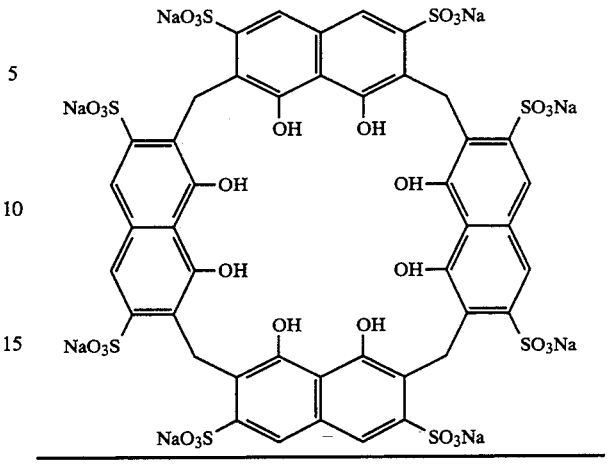

We claim:

1. Apparatus for performing chemical reactions on a continuous basis comprising:
   i) liquid transport and containment means for continuously transporting and containing a chemical reaction having an inlet section, an elongated non-linearly disposed intermediate section and outlet effluent section,
   ii) supply means for continuously feeding a liquid or slurry at a controllably variable rate through the liquid transport and containment means,
   iii) a microwave generator to supply microwave energy to the intermediate section for continuously carrying out a chemical reaction in said intermediate section,
   iv) temperature measurement means associated with the intermediate or effluent sections to measure the temperature of the products of a chemical reaction,
   v) pressure control means associated with said liquid transport and containment means for controlling the pressure of said liquid or slurry therein,
   vi) heat exchange means in the effluent section to cool the effluent feed and entrained reaction products substantially immediately on exit from the intermediate section, and
   vii) control means operatively interconnecting said supply means, said microwave generator, said temperature measurement means and said pressure control means to control the chemical reactions.

2. Apparatus as claimed in claim 1 wherein said control means controls variations in the microwave power level by switching the microwave generator on and off.

3. Apparatus as claimed in claim 1 wherein the heat exchange means is comprised of at least one thermoelectric Peltier cooling pad for controlling the cooling temperature.

4. Apparatus as claimed in claim 1 wherein the inlet section of the liquid transport and containment means comprises means for separately feeding different reactants for mixing within the intermediate section.

5. Apparatus as claimed in claim 1 wherein said control means enables the temperature of a reaction to be set at a predetermined value.

6. Apparatus as claimed in claim 5 wherein the control means also allows the pressure of the liquid or slurry to be set to a predetermined value, the feed rate and microwave power being controllably varied to maintain the pressure and temperature substantially at their predetermined set values.

7. Apparatus as claimed in claim 1, wherein said control means is a microprocessor.

* * * * *